(12) United States Patent
Paul et al.

(10) Patent No.: US 6,755,833 B1
(45) Date of Patent: Jun. 29, 2004

(54) BONE SUPPORT ASSEMBLY

(75) Inventors: Kamaljit S. Paul, 3220 Old Orchard La., Oshkosh, WI (US) 54901; Rodney S. Rogstad, Menominee, WI (US); Troy R. Larson, Menominee, WI (US); Bruce W. Stursa, Sarona, WI (US)

(73) Assignee: Kamaljit S. Paul, Oshkosh, WI (US)

( * ) Notice: Subject to any disclaimer, the term of this patent is extended or adjusted under 35 U.S.C. 154(b) by 93 days.

(21) Appl. No.: 10/014,409

(22) Filed: Dec. 14, 2001

(51) Int. Cl.$^7$ .............................................. A61B 17/56
(52) U.S. Cl. ........................................ 606/70; 606/66
(58) Field of Search .............................. 606/69, 70, 71, 606/72, 66

(56) References Cited

U.S. PATENT DOCUMENTS

| | | | |
|---|---|---|---|
| 2,406,832 A | 9/1946 | Hardinge | |
| 2,486,303 A | 10/1949 | Longfellow | |
| 4,246,660 A | 1/1981 | Wevers | |
| 4,503,848 A | 3/1985 | Caspar et al. | 128/92 |
| 4,513,744 A | 4/1985 | Klaue | |
| 5,324,290 A | 6/1994 | Zdeblick et al. | 606/61 |
| 5,344,421 A | 9/1994 | Crook | 606/61 |
| 5,569,251 A | 10/1996 | Baker et al. | 606/69 |
| 5,578,034 A | 11/1996 | Estes | 606/61 |
| 5,616,142 A | 4/1997 | Yuan et al. | 606/61 |
| 5,616,144 A | 4/1997 | Yapp et al. | 606/61 |
| 5,676,666 A | 10/1997 | Oxland et al. | 606/61 |
| 5,681,311 A * | 10/1997 | Foley et al. | 606/61 |
| 5,728,127 A | 3/1998 | Asher et al. | 606/61 |
| 5,876,402 A * | 3/1999 | Errico et al. | 606/61 |
| 5,904,683 A * | 5/1999 | Pohndorf et al. | 606/61 |
| 5,951,558 A | 9/1999 | Fiz | 606/70 |
| 5,954,722 A | 9/1999 | Bono | 606/61 |
| 6,017,345 A | 1/2000 | Richelsoph | 606/70 |
| 6,030,389 A | 2/2000 | Wagner et al. | 606/71 |
| 6,106,557 A | 8/2000 | Robioneck et al. | 623/17 |
| 6,129,730 A | 10/2000 | Bono et al. | 606/73 |
| 6,139,550 A | 10/2000 | Michelson | 606/69 |
| 6,152,927 A | 11/2000 | Farris et al. | 606/69 |
| 6,159,213 A | 12/2000 | Rogozinski | 606/70 |

(List continued on next page.)

FOREIGN PATENT DOCUMENTS

| | | | |
|---|---|---|---|
| DE | 44 09 833 A1 | 10/1995 | |
| EP | 1169971 | 1/2002 | |
| EP | 1 169 971 | 1/2002 | |
| FR | 1505513 | 11/1966 | |
| FR | 2778088 | 11/1999 | |
| WO | WO 00/24325 | 5/2000 | A61B/17/68 |
| WO | WO 00/64359 | 11/2000 | A61B/17/56 |
| WO | WO 01/26566 | 4/2001 | A61B/17/70 |
| WO | WO 01/26567 A1 | 4/2001 | |

OTHER PUBLICATIONS

"Blackstone™ Anterior Cervical Plate." Blackstone Medical Inc. Product literature. 4 sheets. No date available.
"CSLP Variable Angle: For Use with the Cervical Spine Locking Plate System." Technique Guide. 2000 SYNTHES® Spine. 28 sheets.
Zdeblick, M.D., Thomas A. et al. "Premier™ Anterior Cervical Plate System." Surgical Technique. 2000 Medtronic Sofamor Danek. 30 sheets.
Health Journal, Tara Parker–Pope. The Wall Street Journal, Jan. 2001. 1 sheet.

(List continued on next page.)

Primary Examiner—Pedro Philogene
Assistant Examiner—D A Bonderer
(74) Attorney, Agent, or Firm—Wilhelm Law Service; Thomas D. Wilhelm

(57) ABSTRACT

Novel bone support assembly, and methods of use, wherein a locking member such as a resiliently flexible band, mounted to a bone support plate, automatically and as a consequence of driving a bone fastener through the bone support assembly and into bone structure of a recipient of such bone support assembly, activates a locking feature of the bone support assembly to thereby prevent the bone fastener from withdrawing out of the bone support assembly and past the locking member.

100 Claims, 8 Drawing Sheets

U.S. PATENT DOCUMENTS

| | | | |
|---|---|---|---|
| 6,193,721 B1 | 2/2001 | Michelson | 606/70 |
| 6,224,602 B1 | 5/2001 | Hayes | 606/69 |
| 6,235,034 B1 | 5/2001 | Bray | 606/71 |
| 6,238,396 B1 | 5/2001 | Lombardo | 606/61 |
| 6,241,731 B1 | 6/2001 | Fiz | 606/65 |
| 6,293,949 B1 | 9/2001 | Justis et al. | 606/61 |
| 6,306,139 B1 | 10/2001 | Fuentes | 606/70 |
| 6,364,881 B1 | 4/2002 | Apgar et al. | |
| 6,402,756 B1 | 6/2002 | Ralph et al. | 606/71 |
| 6,454,771 B1 | 9/2002 | Michelson | |
| 6,458,133 B1 | 10/2002 | Lin | 606/69 |
| 6,533,786 B1 | 3/2003 | Needham et al. | 606/61 |
| 6,602,255 B1 | 8/2003 | Campbell et al. | |
| 6,602,256 B1 | 8/2003 | Hayes | |
| 2002/0151899 A1 * | 10/2002 | Bailey et al. | 606/69 |
| 2003/0018335 A1 | 1/2003 | Michelson | |
| 2003/0045880 A1 | 3/2003 | Michelson | |
| 2003/0083658 A1 * | 5/2003 | Hawkes et al. | 606/61 |

OTHER PUBLICATIONS

C–TEK Anterior Cervical Plate, 2001 Interpore Cross International, 1 sheet.

C–TEK Anterior Cervical Plate System, Interpore Cross, Oct. 2000, 1 sheet.

WINDOW Cervical Stabilization System, 2000 Endius, Inc., 10 sheets.

CASPAR Instruments for Anterior Cervical Fusion, AESCULAP, undated, 4 sheets.

NDC Internet Data Sheets, date unknown, 3 sheets.

Ni–Ti alloy Internet Data Sheets, date unknown, 4 sheets.

"Zenith the perfect alliance for successful cervical funsions," Eurosurgical, Spine A Circuit, date unknown, 2 sheets of internet pages, downloaded Apr. 15, 2003.

"ORIA ZENITH Product Specifications," REO Spine Line, Spine Network, Mar. 2003, 18 sheets.

Aesculap(R) Advanced Biomechanical Concept, product literature, date unknown, 11pages.

Interpore Cross, Spinal Products, product literature, date 2002, 7 pages.

Zenith, Eurosurgical, internet product literature, date unknown, 2 pages.

Zenith, Oria, internet product specifications, date unknown, 18 pages.

Blackstone, Anterior Cervical Plate, product literature, date unknown, 4 pages.

Synthes, CSLP Variable Angle, product literature, date 2000, 28 pages.

Zdeblick, Thomas a et al, Premier (TM) Anterior Cervical Plate System, Medtronic, surgical technique, date 2000, 30 pages.

The Wall Street Journal—New Procedure Makes Spinal–Fusion Surgery Less Taxing on Patient, Health Journal, Jan. 5, 2001, 1 page.

Interpore Cross, Any Way You Place It, C–Tek Spells Cervical Technology, product literature, date 2001, 2 pages.

The Market for Spinal Implants—Internet Website, date unknown http://www.crossmedical.com/spinal.html, 4 pages.

* cited by examiner

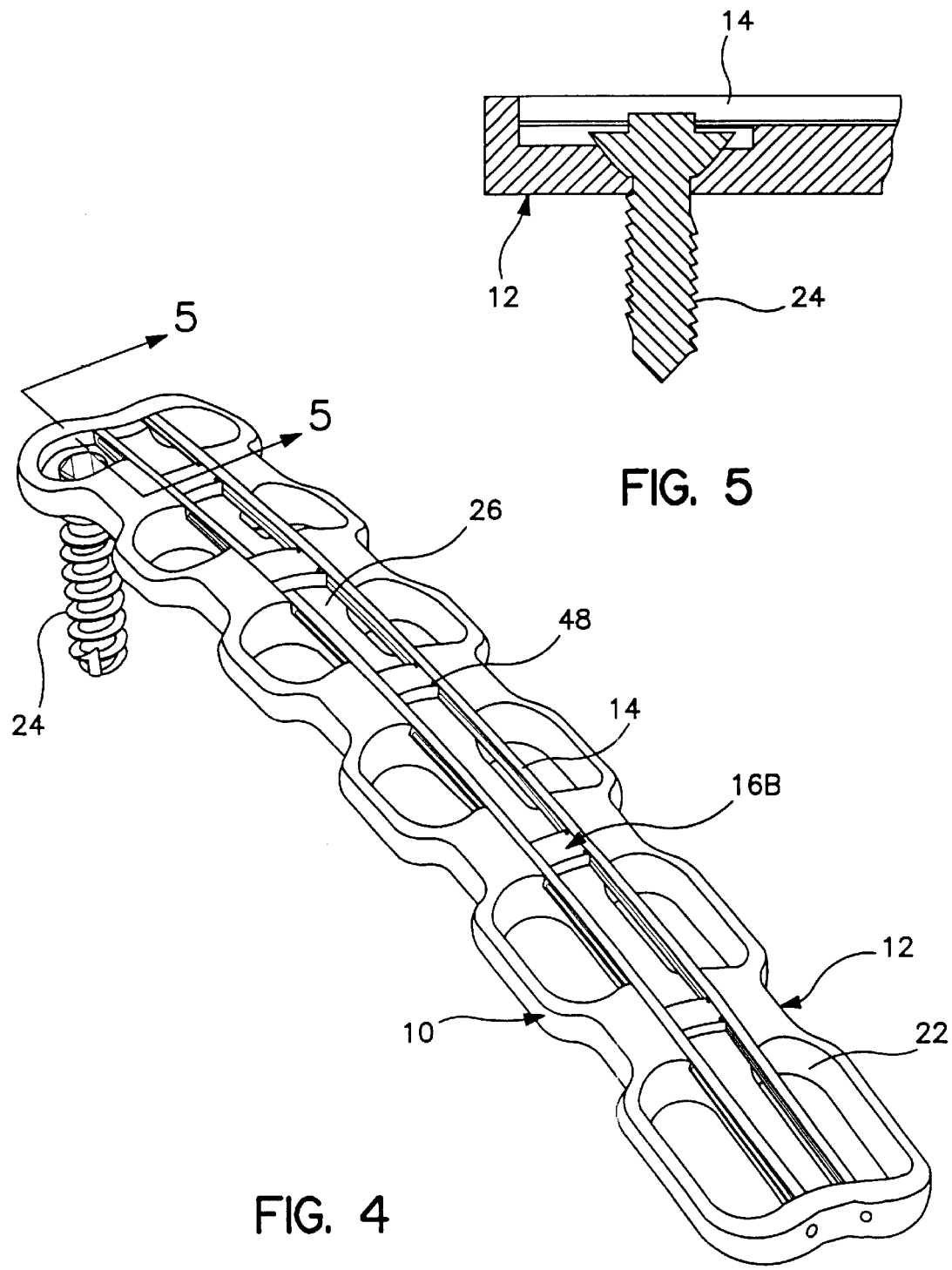

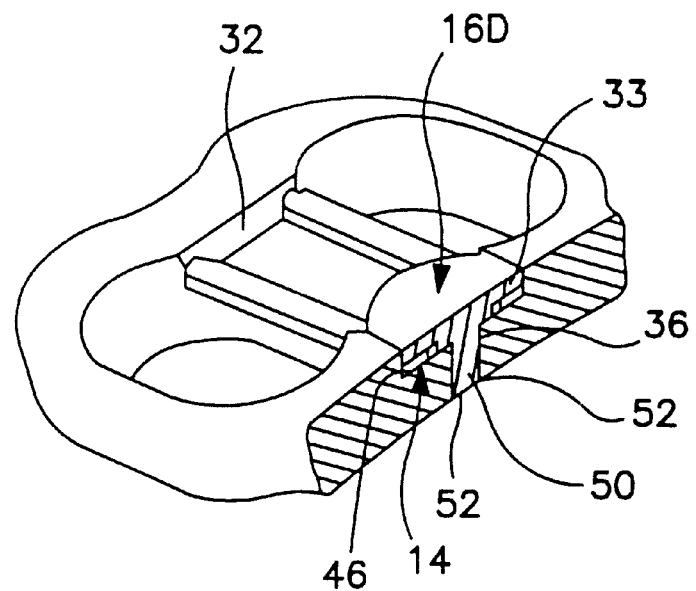
FIG. 13
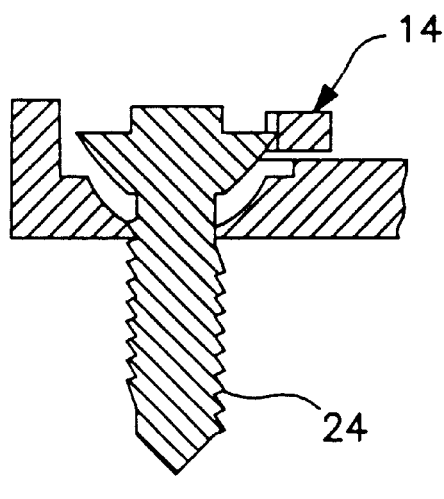
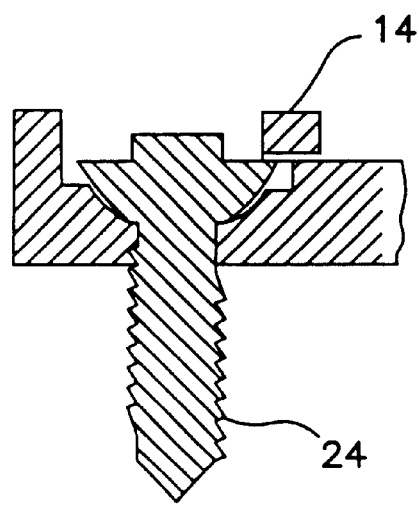
FIG. 5A          FIG. 5B

BONE SUPPORT ASSEMBLY

BACKGROUND

The present invention relates to devices for the fixation and/or support of bones. In particular, the present invention relates to a bone support assembly, and a corresponding bone support plate, for the fixation and/or support of bones of the spinal column. The plate of the present invention has particular application in situations where compressional or "settling" forces, as well as torsional and flexing forces, of "fixed" vertebrae on a spinal plate cause significant stressing and potential failure of the spinal plate and/or plate components.

Vertebral fixation has become a common approach to treating spinal disorders, fractures, and for fusion of vertebrae at the time such fixation is instituted. Namely, one or more vertebrae are fixed in position relative to one or more other vertebrae above and/or below the vertebrae to be fixed. Generally, a spinal plate is the device of choice used for mechanically supporting such vertebral fixation. A typical spinal plate includes a plate having a plurality of apertures therethrough. A corresponding plurality of fasteners, i.e., bone screws, are generally positioned into and through respective apertures of the plate to secure the spinal plate to a bone, such as two respective upper and lower supporting adjacent spinal vertebrae. The screws are fastened to the respective support vertebrae to secure the spinal plate to the respective vertebrae. In general, such plate and screw assemblies can be utilized, generally, for anterior fixation of the spine for cervical, lumbar, and/or thoracic fixation.

The basis of anterior fixation or plating is to approach the spine from an anterior or anterio-lateral approach, and use the screws to solidly mount the spinal plate to the affected vertebrae. Often, in addition to the application of a spinal plate, graft material may be combined in an attempt to permanently fuse together adjacent vertebrae. The graft material can consist of bone grafts obtained from bones of the recipient or another individual.

A common problem associated with the use of such spinal plates is the tendency of the bone screws to "back out" or pull away or withdraw from the bone into which they are fixed. This problem occurs, primarily, due to the normal torsional and bending motions of the body and spine. This is a particularly important problem because as the screws become loose and pull away or withdraw from the bone, the heads of the screws can rise above the surface of the spinal plate and, possibly, even work their way completely out of the bone. While this condition can cause extreme discomfort for the recipient, this condition can also create a number of potentially serious physiological problems given the significant amount of nervous and vascular structures associated at or near the potential locations of anterior spinal plate fixations.

A number of designs have been proposed in attempts to prevent screws from pulling away or withdrawing from the bone and/or to prevent the screws from backing out or pulling away or withdrawing from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments including potential for breakage or requiring particular precision and alignment in their application in order to work correctly. Additionally, loose components and accessories of spinal plates which address the "backing-out" or withdrawal problem can get dropped and/or misplaced while the vertebral fixation surgical procedure is taking place, prolonging and complicating the procedure as well as creating substantial risk of harm to the recipient.

Yet another common problem associated with the use of such spinal plates is the tendency of the vertebrae being "fixed" to settle after spinal plate insertion adding compression forces to the above-listed forces which cause the bone screws to "back out" or pull away or withdraw from the bone into which they were fixed.

It is an object of the invention to provide bone support assemblies which provide rigid bone-to-bone fixation and/or support, such as e.g. adjacent or second adjacent vertebrae, while allowing post-procedural compression between the respective bones.

It is another object of the invention to provide bone support assemblies which afford substantial protection against pulling away or withdrawal of affixing components which may result from torsional movement, flexing movement, or stress and/or dynamic load sharing of the vertebrae, thereby enhancing the bone rebuilding process.

It is yet another object of the invention to provide bone support assemblies which attenuate application of stress on the apparatus and affixing components It is a further object of the invention to provide bone support assemblies comprising a bone support plate and resiliently flexible bands so mounted and positioned to enable bone fasteners to pass such bands when being installed in a recipient and which prevent withdrawal of such bone fasteners after installation in the recipient.

It is yet a further object of the invention to provide bone support assemblies which can be completely pre-assembled such that no assembly steps need be performed on the bone support assembly during installation of such bone support assembly in a recipient thereof.

It is still a further object of the invention to provide bone support assemblies wherein apparatus, in such bone support assemblies, for preventing withdrawal of bone fasteners from the bone, after installation on a recipient, are automatically activated, to prevent such withdrawal, as a consequence of the installation of the bone fasteners.

SUMMARY

This invention provides a novel bone support assembly, and methods of use, wherein a locking member such as a resiliently flexible band, mounted to the bone support plate, automatically and as a consequence of driving a bone fastener through the bone support assembly and into bone structure of a recipient of such bone support assembly, activates a locking feature of the bone support assembly to thereby prevent the bone fastener from withdrawing out of the bone support assembly and past the locking member.

Thus, the invention comprehends a bone support assembly, comprising a bone support plate. The bone support plate comprises a top surface, a bottom surface opposite the top surface and adapted to engage bone structure of a recipient, a plurality of bone-fastener-receiving apertures for receiving bone fasteners therethrough for securing the bone support assembly to the bone structure of the recipient. The bone support assembly further comprises a locking member mounted to the bone support plate, the locking member being effective, when a bone fastener is driven through an aperture into bone structure of a recipient, to automatically and as a consequence of driving the bone fastener, activate a locking feature of the bone support assembly effective to prevent the bone fastener from withdrawing out of the bone support assembly and past the locking member.

In preferred embodiments, the locking member comprises a resiliently flexible band. A length of the band extends along a side of one or more corresponding ones of the apertures whereby, as the bone fastener is driven, a break structure of the bone fastener, such as a screw head, can urge the band to automatically flex transversely of the length of the band, from a first flexural condition, until the break structure in the bone fastener is driven past the band, whereupon the band returns to the previous flexural condition and overlies the break structure of the so-driven bone fastener and thereby prevents the bone fastener from withdrawing.

Also in preferred embodiments, the bone support plate further comprises a channel defined in and as part of the top surface of the bone support plate. The channel has side walls opening into and extending alongside ones of the plurality of bone-fastener-receiving apertures. The resiliently flexible band is disposed in the channel and extends along a side of the channel.

The channel preferably has a bottom surface.

In some embodiments, at least all except two of the bone-fastener-receiving apertures comprise slots, enabling longitudinal movement of bone fasteners in the slots, with respect to the bone support plate, and first and second ones of the bone-fastener-receiving apertures can comprise circular openings.

In preferred embodiments, all of the bone-fastener-receiving apertures comprise slots, having lengths greater than respective widths of the slots.

Preferably, the flexible band extends along substantially a full length of the bone support plate.

The bone support assembly preferably includes a second flexible band and the first and second flexible bands extend along substantially full lengths of respective first and second sides of the channel, the first and second flexible bands collectively extending along the sides of all of the bone-fastener-receiving apertures.

The bone support assemblies preferably comprise one or more band retainers mounted to the bone support plate, and mounting the flexible band to the bone support plate.

In some embodiments, the band retainers mount the bands to the plate with abutment of the retainer against the flexible bands and urging of the flexible bands against respective first and second sides of the channel through such abutment.

In other embodiments, a retainer comprises a stud extending through the retainer-receiving aperture, the stud being welded to the bone support plate adjacent the bottom surface of the bone support plate.

Compositions of the flexible band preferably comprise predominantly nickel and titanium. Preferred compositions of the flexible bands comprise about 55 percent by weight to about 56 percent by weight nickel and about 44 percent by weight to about 45 percent by weight titanium.

The compositions of flexible bands of the invention preferably comprise shape memory metal alloys, which can be predominantly nickel and titanium, although other materials can be used so long as the material has the requisite flexural properties, has suitable strength properties, and is safe for use in living body surgical procedures.

In preferred embodiments, the bone support plate is elongated. The bone-fastener-receiving apertures are arrayed in first and second rows along a length of the bone support plate. The bone support assembly further comprises a second resiliently flexible band, and the first and second bands are mounted at the opposing side walls of the channel, and extend along a portion of the length of the channel occupied by the bone screw apertures.

In preferred embodiments, first and second bands are mounted to the bone support plate by at least one band retainer, preferably a plurality of band retainers, displaced from the apertures, and the first and second bands can flex at respective slots about mounting loci displaced longitudinally along the bone support plate from respective ones of the bone screw apertures, when bone screws are driven through the bone support plate and respectively past respective edges of the bands.

The invention further comprises a method of mounting a bone support to bone structure. The method comprises providing a bone support assembly, comprising a bone support plate, having a top surface, a bottom surface opposite the top surface and adapted to engage bone structure of a recipient, and a plurality of bone-fastener-receiving apertures for receiving bone fasteners therethrough for securing the bone support assembly to such bone structure of such recipient, and one or more resiliently flexible bands mounted to the bone support plate, a length of the band extending along sides of corresponding ones of the apertures. The method further comprises driving a bone fastener through a respective bone-fastener-receiving aperture and including driving a break structure of the bone fastener past the flexible band such that the break structure of the fastener causes the flexible band to flex transversely of the length of the band, from an unflexed condition, as the break structure of the bone fastener passes the band whereupon, when the break structure of the fastener moves past the flexible band, the resiliently flexible band returns to the unflexed condition and overlies the break structure of the so-driven bone fastener, thereby preventing the bone fastener from withdrawing out of the bone support assembly past the resiliently flexible band.

In preferred embodiments, the method includes driving a plurality of bone fasteners through respective bone-fastener-receiving apertures in the bone support plate, including driving each bone fastener a sufficient distance toward the bone support plate that a break structure on the respective fastener passes the flexible band whereby the flexible band flexes over the break surface of the fastener and thereby prevents the bone fastener from withdrawing out of the bone support assembly past the resiliently flexible band.

BRIEF DESCRIPTION OF THE DRAWINGS

FIG. 4 shows a pictorial view of a second embodiment of bone support assemblies of the invention.

FIG. 5 shows a cross-section of the bone support assembly of FIG. 4, taken at 5—5 of FIG. 4.

FIG. 5A is a cross-section as in FIG. 5, but at a 90 degree angle from the cross-section of FIG. 5, thus looking along the length of the bone support plate, and showing the resiliently flexible band flexed by passage of the head of a bone screw.

FIG. 5B is a cross-section as in FIG. 5A wherein the head of the bone screw has passed the bottom of the flexible band thus to enable the resiliently flexible band to revert to its unflexed condition over the head of the bone screw.

FIG. 13 is a cross-section of the bone support assembly of FIG. 11, taken at 13—13 of FIG. 11.

Figure 2:
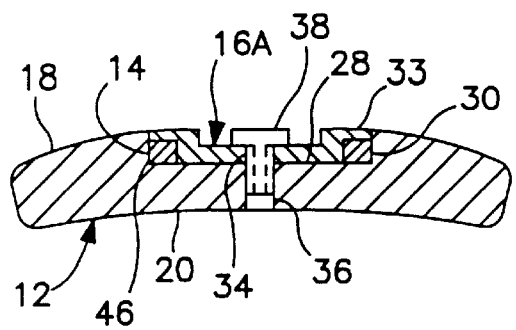
FIG. 2 shows a cross-section of the bone support assembly of FIG. 1, taken at 2—2 of FIG. 1.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1:
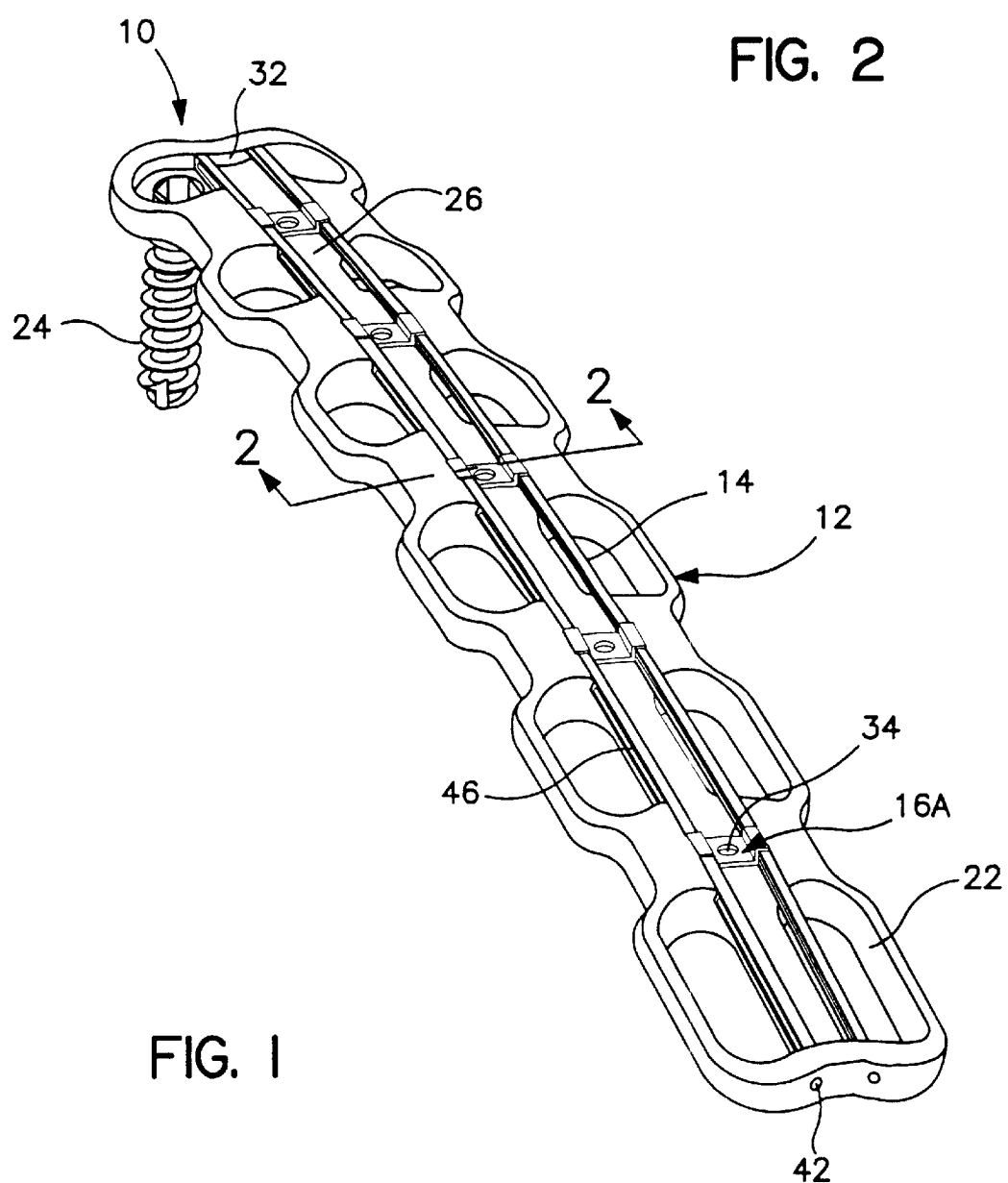
FIG. 1 shows a pictorial view of a first embodiment of bone support assemblies of the invention.
Figure 3:
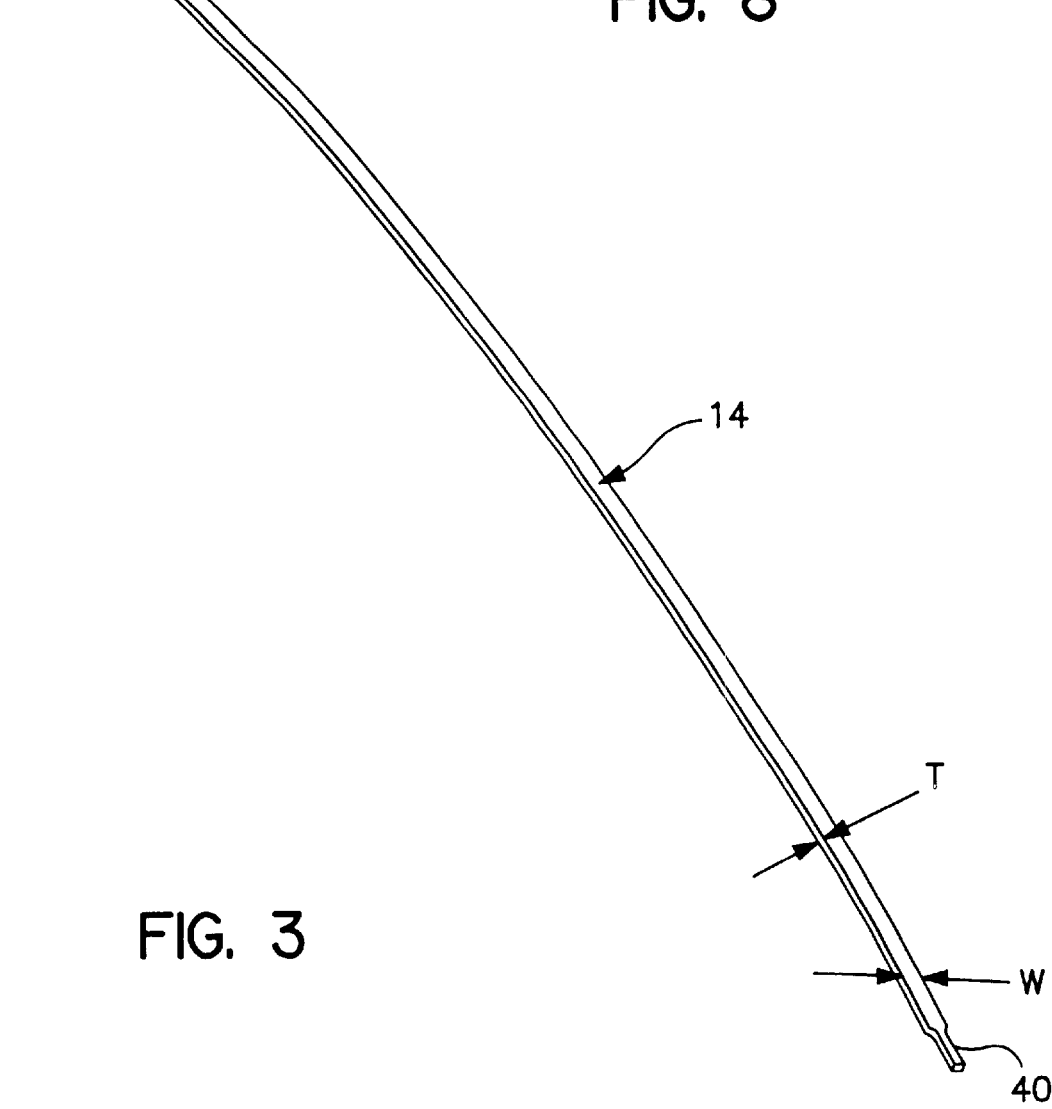
FIG. 3 shows a pictorial view of a flexible band used in bone support assemblies of the invention.

Referring now to the embodiments illustrated by FIGS. 1–3, a bone support assembly 10 of the invention includes a bone support plate 12, a resiliently flexible band or locking member 14, and a band retainer 16A.

Bone support plate 12 has a top surface 18, a bottom surface 20, and a plurality of bone-fastener-receiving apertures 22 which receive bone fasteners such as bone screws 24. Apertures 22 are arranged in first and second rows of such apertures, along the length of the plate.

Figure 9:
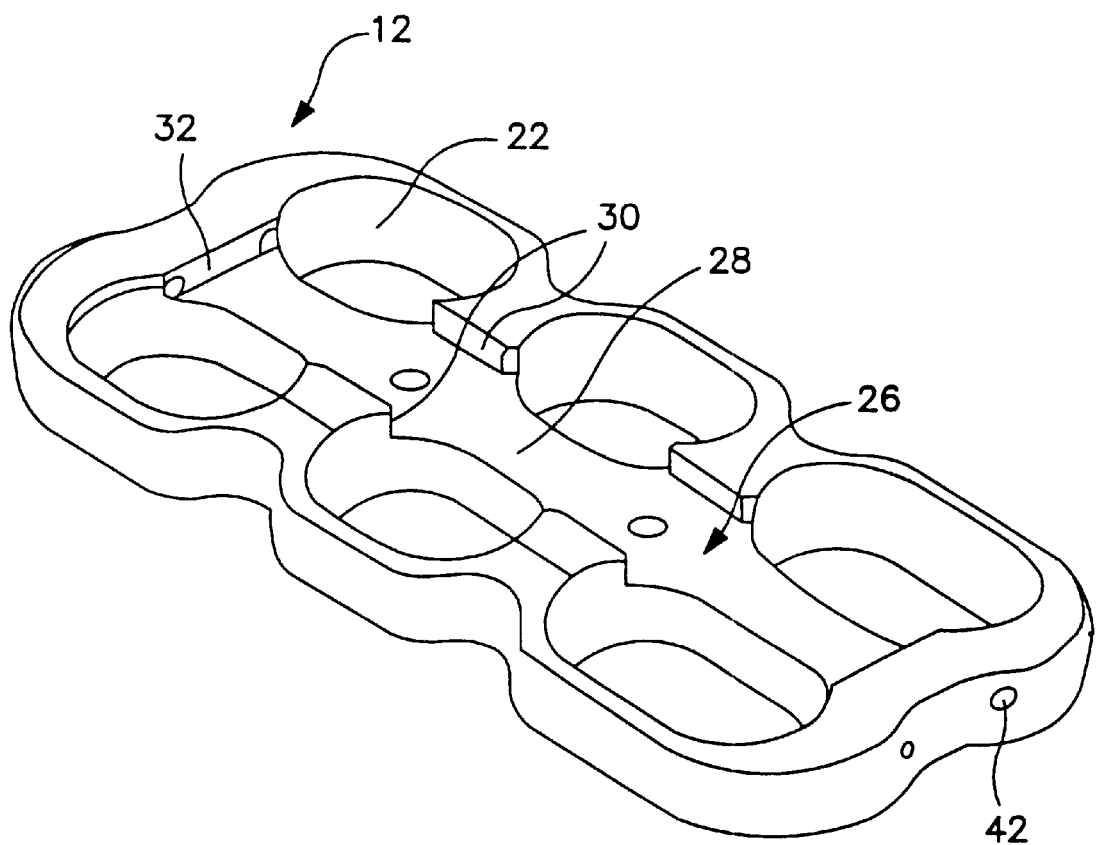
FIG. 9 shows a pictorial view of a bone support plate used in a fourth embodiment of bone support assemblies of the invention.

Top surface 18 of the bone support plate defines a channel 26 extending along the length of the support plate. Channel 26 has a bottom wall 28, opposing side walls 30, best seen in FIG. 9, and opposing end walls 32, also best seen in FIG. 9.

Returning now to the embodiments specifically represented by FIGS. 1 and 2, retainer 16A has a pair of flanges 33, each of which extends over one of the resiliently flexible bands 14 at a location displaced from respective adjacent apertures 22, whereby the respective band is trapped between the bottom surface 28 of the channel, the respective side surface of the channel, and the respective flange 33 of the retainer. Retainer 16A includes an aperture 34. An aperture 36 in the bone support plate underlies aperture 34 in the retainer. A locking screw 38 extends through aperture 34 and into aperture 36, securing retainer 16A to the bone support plate. Preferably, the retainer is sized and configured, in combination with the side and bottom walls of the channel, to apply substantial e.g. side and/or top loading pressure against the band thereby to effectively prevent movement of the band with respect to the bone support plate at the location of the retainer.

Bands 14 have reduced cross-section ends 40. End walls 32 of the bone support plate include apertures 42 for receiving the reduced cross-section ends 40 of the bands. Band ends 40 are accordingly received in apertures 42, thereby restraining the bands against longitudinal movement in the bone support assembly, as well as restraining the bands against transverse lateral movement at the end walls.

While bands 14 are effectively prevented from moving laterally at retainers 16A, and are prevented from moving laterally at end walls 32, as well as being prevented from moving longitudinally at end walls 32, the compositions of bands 14 are selected such that the band material, itself, has a great degree of resilient flexural capacity. Accordingly, at locations displaced from such restraint as applied at retainers 16A and end apertures 42, e.g. at apertures 22, the bands can readily flex in directions transverse to the lengths of the bands. Thus, in response to respective forces, portions of bands 14 which are relatively displaced from retainers 16A and end apertures 36 can be moved along the width of plate 12, or upwardly from the plate. Such movement is, of course, limited by the restraints imposed periodically along the lengths of the bands by retainers 16A and end apertures 36.

Side walls 30 of the channel are specifically located and configured so as to open into the sides of, and extend along and inwardly of the sides of, apertures 22. In general, imaginary extensions of side walls 30 project across apertures 22 at locations displaced inwardly of the aperture side walls by about 1 mm. Retainers 16A are so sized and configured that when the retainers are installed, end surfaces 44 of the retainers abut the bands with sufficient close tolerance fit that the end surfaces 44 urge the bands solidly against the side walls of the channels. Thus, retainers 16A position bands 14 solidly against the side walls of the channels where the bands are not passing over apertures 22. With the bands solidly against the side walls of the channel, the outwardly-disposed sides 46 of the bands are in surface to surface contact with side walls 30 of the channels. The outwardly-disposed sides 46 of the bands, the respective rows of apertures 22, and retainers 16A are thus correspondingly sized, arranged and configured with respect to each other, that when bands 14 are trapped between the side walls, the channel bottom, and the retainers, the bands, when at rest, extend along a path wherein the outwardly-disposed sides of the bands extend closely beside the side walls of the channel. Since imaginary extensions of the side walls are displaced inwardly of the aperture side walls by about 1 mm, the outwardly-disposed side walls of the bands also are displaced inwardly of the aperture side walls by about 1 mm.

FIGS. 4 and 5 illustrate a second family of embodiments of the invention. In these embodiments, all elements of the invention are the same as in the embodiments of FIGS. 1 and 2, except for the retainer and its interactions. While retainer 16A in FIGS. 1 and 2 is held in place with a locking screw 38, and has flanges 33 interfacing with the tops of bands 14, in the embodiments of FIGS. 4 and 5, retainers 16B are disposed in abutting relationship with bands 14, and are spot welded at welds 48 to bands 14. Further, retainers 16B have studs (not shown in FIGS. 4–5) which extend through respective apertures corresponding to apertures 36 in plate 12 of FIGS. 1 and 2. Studs (not shown in FIGS. 4–5) extend through the plate apertures and are spot welded to the plate at the bottom wall of the plate. Such apertures, studs, and spot welds are shown in e.g. FIGS. 6 and 7, discussed following.

Thus, the retainers of FIGS. 4 and 5 interact with the bands through the abutment interface in combination with the spot welds between the bands and the retainers, and use the abutment interface, in combination with close fit tolerances, to urge the bands into frictional engagement with the side walls of the channel.

FIGS. 5, 5A, and 5B illustrate the process by which a band 14 is flexed when a bone screw 24 passes the band, and further illustrate the interference in a withdrawal path of the screw, provided by the band after the screw has been driven past the band and the band has returned to the less flexed or unflexed condition.

Figure 8:
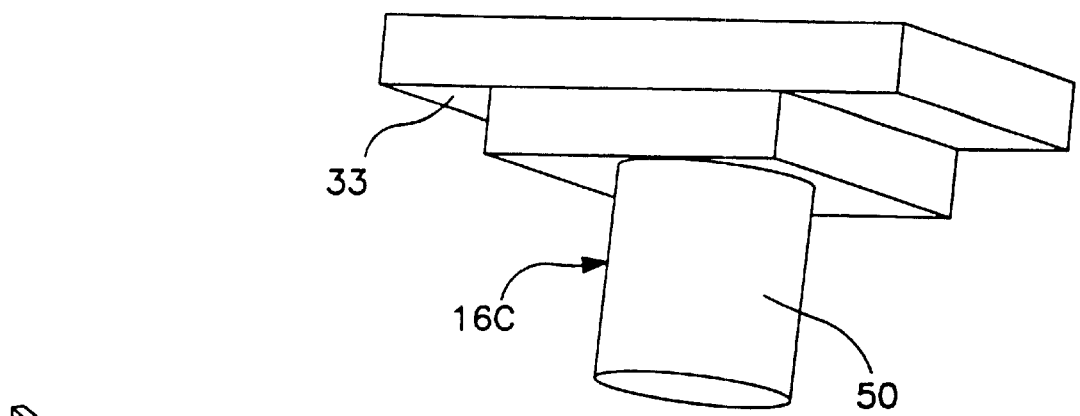
FIG. 8 shows a pictorial view of a retainer used in the bone support assembly illustrated in FIG. 6.
Figure 7:
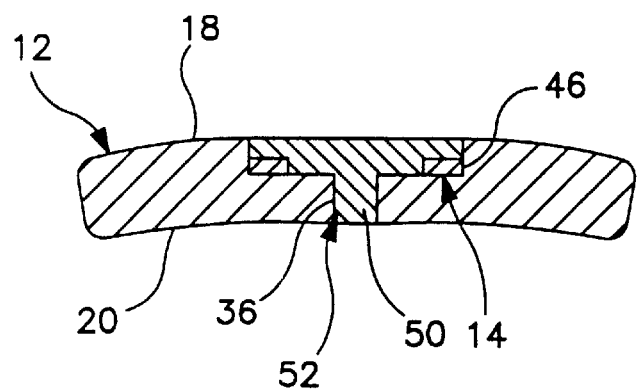
FIG. 7 shows a cross-section of the bone support assembly of FIG. 6, taken at 7—7 of FIG. 6.
Figure 6:
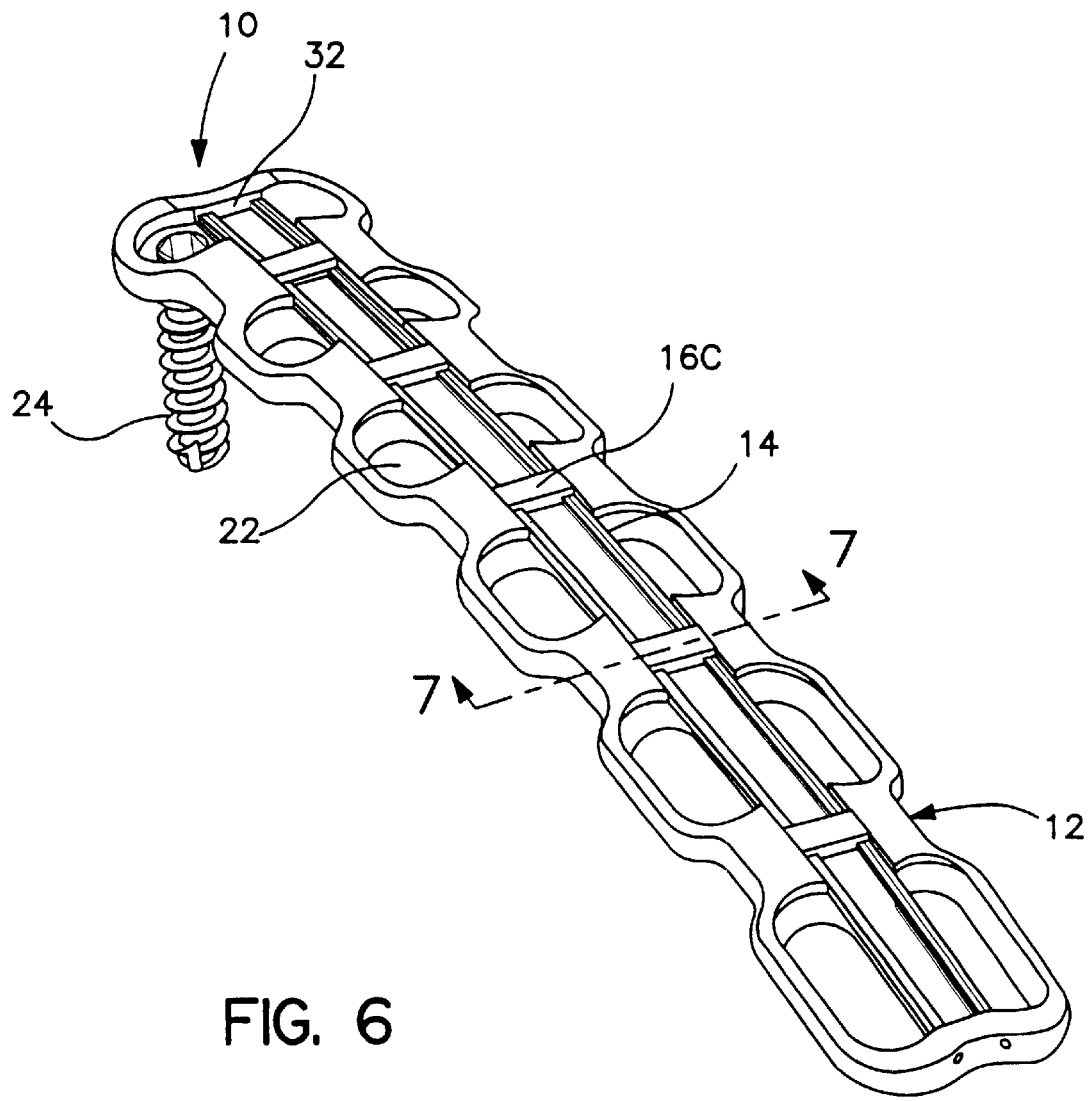
FIG. 6 shows a pictorial view of a third embodiment of bone support assemblies of the invention.

FIGS. 6–8 illustrate a third family of embodiments of the invention. In the embodiments of FIGS. 6–8, all elements of the invention are the same as in the embodiments of FIGS. 1–5, except for the retainer and its interactions. Retainer 16A in FIGS. 1 and 2 has a flange 33 which overlies bands 14, and is secured to plate 12 with a locking screw 38. Retainer 16B in FIGS. 4 and 5 interacts with bands 14 by abutment, fortified by spot welds, and is secured to plate 12 with spot welds. In the family of embodiments represented by FIGS. 6–8, retainer 16C has flanges 33 (best illustrated in FIG. 8) which overlie bands 14 as in FIGS. 1 and 2 and has a stud 50 extending through aperture 36 in plate 12. Stud 36 is spot welded to plate 12 by welds 52 at bottom surface 20 of the plate. Accordingly, the securement to the plate is by spot welds displaced from apertures 22 and from bands 14. Interaction between bands 14 and retainer 16C is through an overlying flange 33 of the retainer, whereby the bands are not subjected to the direct thermal affects of the spot welding process.

FIGS. 9–13 illustrate a fourth family of embodiments of the invention. In the embodiments of FIGS. 9–13, all elements of the invention are the same as in the previous embodiments except for the retainer and its interactions, and the length of number of apertures and corresponding length of plate 12. As seen therein, the plate in FIGS. 9–13 has only 3 bone screw receiving apertures 22 in each of the two rows of apertures. Retainer 16D, like retainer 16C has flanges 33 which overlie the bands. However flanges 33, seen especially in FIGS. 11 and 13, of retainers 16D have generally round configurations, and extend generally the full length of a portion of the channel side wall between respective ones of the apertures 22, while having straight-line edges at the side walls. Such increased flange footprint provides, in flange 33 of e.g. FIG. 11, controlling interaction over an increased fraction of the length of the bands between apertures 22, as compared to the previous embodiments, whereby control of transverse movement of the bands is extended to substantially the full length of that portion of the side wall which extends between adjacent ones of apertures 24. Retainer 16D has a stud 50 which extends through an aperture 36 in the plate and is spot-welded at welds 52.

Figure 10:
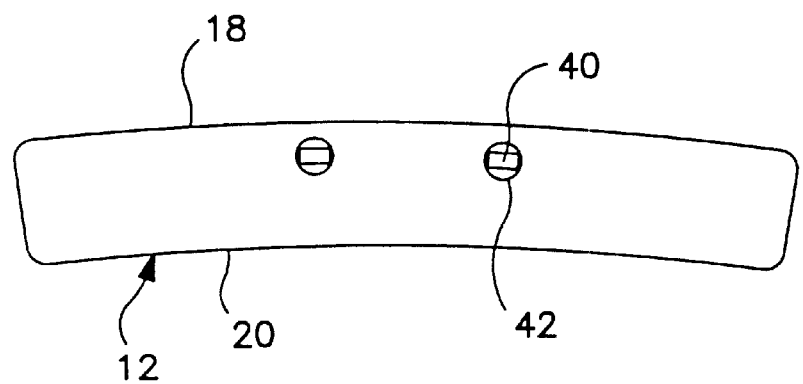
FIG. 10 is an end view of the bone support plate illustrated in FIG. 9.
Figure 11:
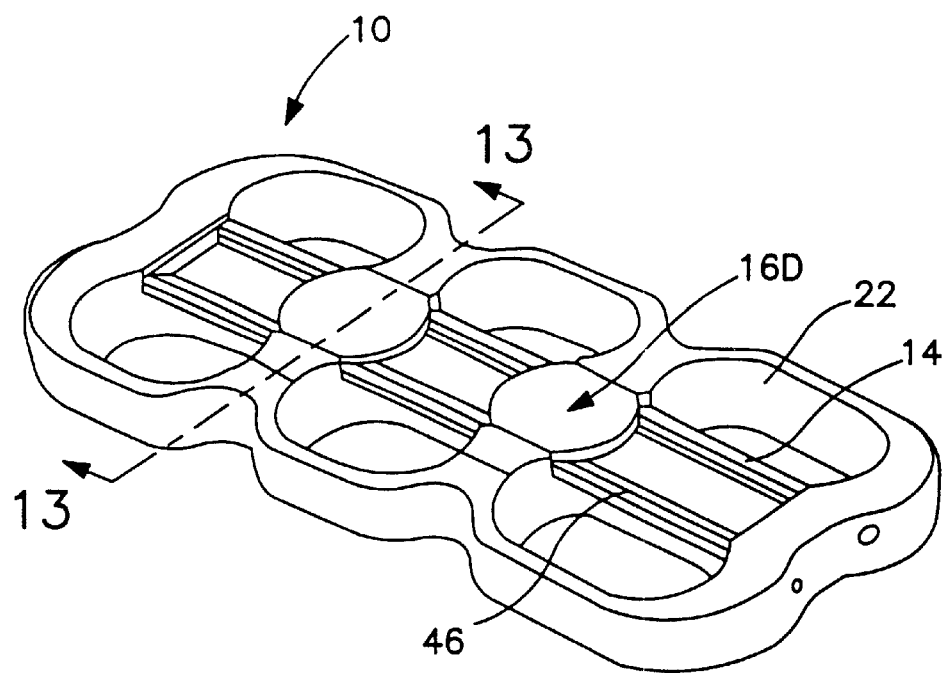
FIG. 11 shows a pictorial view of a bone support assembly of the invention employing the bone support plate of FIG. 9.

FIG. 10 illustrates the reduced cross-section ends 40 of bands 14 in end apertures 42, wherein the relatively larger cross-section main bodies of the bands are restrained against longitudinal movement by interaction with the inner surfaces of end walls 32.

Figure 12:
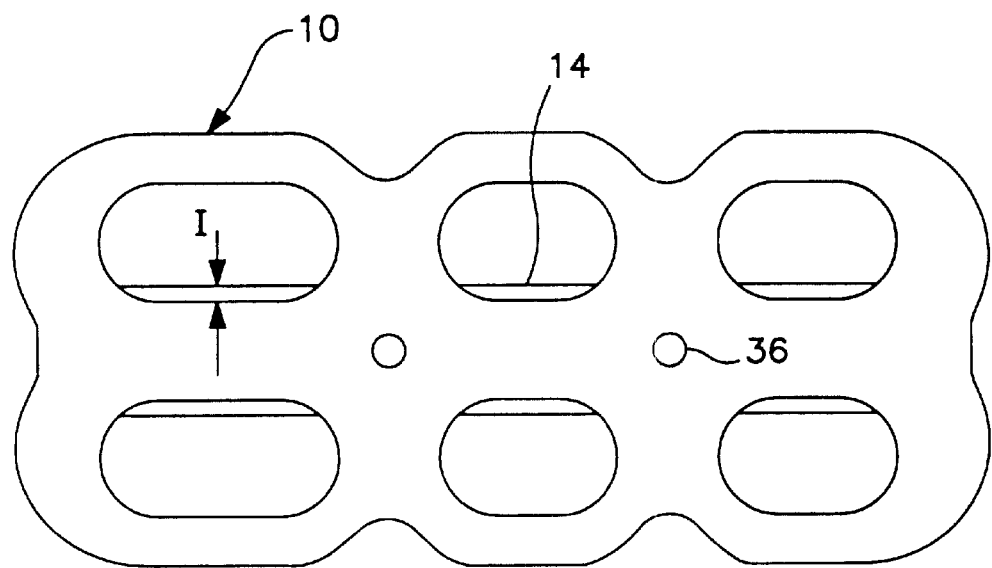
FIG. 12 shows a bottom view of the bone support assembly of FIG. 11, illustrating the flexible bands overlapping the open aperture area of the bone-fastener-receiving slots.

FIG. 12 illustrates a bottom view of assembly 10, directly illustrating the interference path set up by bands 14, to interfere with properly fitting bone screws, adjacent the inner edges of apertures 22. As indicated above, a preferred interference dimension "I", between the side of the aperture and the edge of the respective band, is approximately 1 mm. Such interference dimension can, of course, be different, depending on a variety of parameters relating to the specific structural and operating environments, including the relative configurations of the bone screw, the aperture, and the band. What is important is that the interference be of sufficient dimension, and that the interfering surfaces be so cooperatively configured, that the band effectively interferes with the bone screw so as to prevent the bone screw from withdrawing from assembly 12 without intentional provision for such withdrawal.

Figure 14:
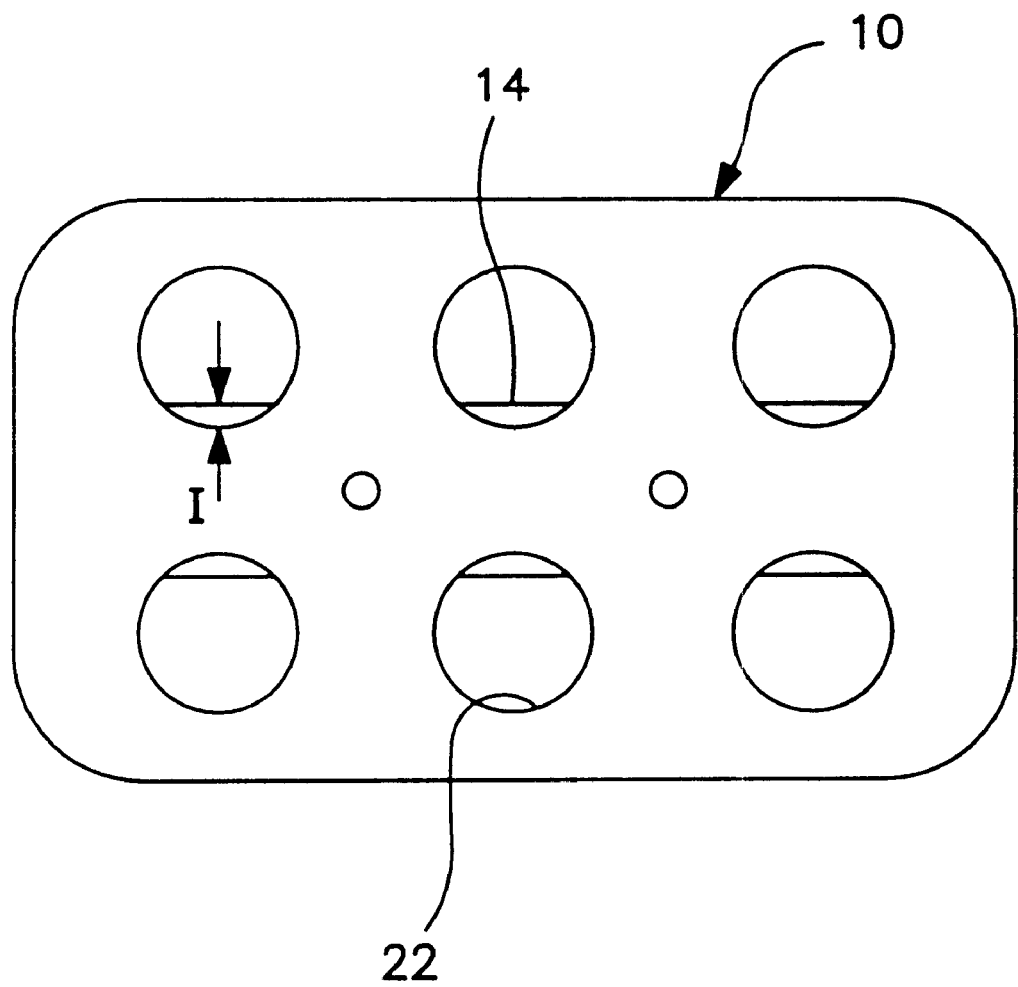
FIG. 14 shows a bottom view of a bone support assembly wherein all the apertures are circular.

FIG. 14 illustrates a bottom view of a fifth family of embodiments of assembly 10 wherein all of apertures 22 are circular. Such support plate assemblies have limited or no freedom of movement with respect to the bone structure to which the assembly is attached for support. Such support plate assemblies are desirable where the bone positions may be desirably fixed with respect to each other.

As illustrated in the drawings, bands 14 extend into respective apertures 22 along substantially less than all of the perimeter of the respective aperture; and bands 14 extend away from the aperture e.g. along channel 26. Further, the bands are mounted to plate 12 at loci displaced from the aperture, and lengths of the bands extend away from respective apertures 22, as at retainers 16 which are located between pairs of apertures 22.

Since bone support assemblies of the invention are to be used within living bodies, all materials used in the bone support assemblies must be compatible with, and safe for use inside, the living body. In that regard, preferred material for bone support plate 12 and retainers 16A is titanium. Preferred compositions for bands 14 having the desired level of resilient flexural capability are shape memory metal alloys, also known as superelastic alloys. Such metals are well known for the ability to tolerate levels of flex which are extraordinary for metals, and to automatically and resiliently return to a pre-flex configuration or condition when the flexing force is released. Thus, lengths or bands of such materials, which have a rest condition or configuration, can be bent, twisted, distorted, and otherwise reconfigured under reconfiguring force and, when the force is removed, will return to the rest configuration or condition, or to a configuration or condition very near to the rest condition or configuration.

Typical shape memory metal alloy bands or superelastic bands are about 50 weight percent to about 60 weight percent nickel and respectively about 50 weight percent to about 40 weight percent titanium, preferably about 55 weight percent to about 56 weight percent nickel and conversely about 45 weight percent to about 44 weight percent titanium. Suitable band materials, containing about 55.8 weight percent nickel and correspondingly about 44.2 weight percent titanium, are available from NDC Company, Wayzata, Minn. as NITINOL SE 508. A typical NITINOL band for use in bone support assemblies used in adults has a width "W" of 0.04 inch (1 mm) and a thickness "T" of 0.016 inch (0.4 mm). Width of the band at ends 40 is reduced to 0.02 inch (0.5 mm) for receipt into end apertures 42.

While shape memory metal alloys are preferred for use in bands 14, other materials can be used so long as such materials meet the requirements of the use environment. Namely, such materials must be safe for use in the living body. Safety is typically controlled by composition and structure. In this analysis, exemplary structure is shown in the drawings herein; and composition is the variable being analyzed.

In addition, such materials, even though not known as shape memory metal alloys, must perform the required physical functions of flexing enough, when properly positioned over apertures 22, to let the bone screws pass below the bands without exceeding the flexural limit of the band material, and returning to a blocking position over the screw after passage of the bone screw. Such flexural properties are based on physical properties inherent in the material composition, in combination with the physical cross-section of the bands.

Thus, certain materials which are not known as shape memory materials can, when fabricated into sufficiently small cross-sections, perform the desired resiliently flexural function. Applicants contemplate that bands 14 can thus employ titanium compositions or stainless steel compositions, as alternatives to the shape memory e.g. NITINOL compositions mentioned above. Other materials can be used so long as such materials satisfy the above safety and performance requirements.

The bone support plates illustrated herein have closed end channels 26 which are closed at end walls 32, with apertures 42 extending through the end walls of the channels. The invention also contemplates bone support plates wherein the channels extend the entire lengths of the plates, and are thus open ended channels (not shown). Where open ended channels are used, end retainers (not shown) are employed to close off the ends of the channels. Such end retainers include end apertures corresponding to apertures 42, whereupon the combination of the open channel and the closing end retainers result in the same, or very similar, channel cross-section configuration at the ends of plate 12.

Channel 26 has a width sized so that the side walls extend into apertures 22 a distance sufficient to generate an interference between bands 14 and apertures 22 when the bands are disposed against side walls 30 and are in relatively less-flexed, or unflexed conditions. Channel 26 has a depth sufficient to accommodate the thicknesses of bands 14. In a family of embodiments (not shown), channel 26 can be intermittent, and exist only adjacent apertures 22. In such embodiments, bands are held in slots defining the band paths. Retainers 16 are not needed, and the functions of the retainers is provided by plate material between the band-holding slots where the channel has been interrupted.

As a result of the structures of the apertures, the channel side walls, the retainers, and the bands, when a bone screw, which properly fits the apertures 22, is driven through an aperture 22, the head of such bone screw impacts the respective band 14 as shown in FIG. 5A, and forces the band in a width-wise transverse direction away from the aperture in order that the head of the bone screw can pass the band. Since the band is readily and resiliently flexible, the band flexes in response to the urging of the head of the bone screw, as shown in FIG. 5A. When the head of the bone screw passes below the bottom of the band, the band is no longer being held in the flexed condition, and returns to the previous condition of being unflexed, thereby setting up a potential interference between the band and the screw, of 1 mm, which interference is activated if and when the screw begins to back out of, or withdraw from, the bone plate.

The invention contemplates that bands 14 can be arranged in other than a rest, or straight, condition when not being forced sideways. Thus, the bands can be under a degree of constant flexural stress, which is increased as the head of the screw passes, and then reverts to the previous level of lesser stress after the screw head passes.

If desired, some break structure other than the head of the screw can be used to activate and release the band. For example, break structure (not shown) can be designed into the screw below the head, above the head, or otherwise, for the purpose of activating the flexural and release properties of the band.

Whatever the positions of the band, whatever the break structure on the screw which interfaces with the band, once the band is released from the flexing of the respective break surface of the screw, and the band thus returns to the lesser stress flex condition, the band is positioned above, over, and in an interfering path with some portion of the screw during withdrawal of the screw from the bone support assembly. Referring to FIGS. 5 and 5B wherein the head of the screw has passed below the bottom of the band, and wherein the band has thus returned to the unflexed condition, the band is seen to overlie a portion of the surface of the head of the screw, such that if the screw begins to withdraw e.g. upwardly from the plate, the head of the screw impacts the bottom of the band. When the screw impacts the bottom of the band, the band, being supported by respective retainers 16A, 16B, 16C, 16D, prevents the screw from further withdrawal from the plate.

As seen in FIG. 5A, when the screw is driven through the plate, e.g. and into bone material of a recipient of such bone support assembly, the force applied by the upwardly-extending angular bottom surface of the screw automatically pushes the band aside as the head of the screw impacts and passes the band. Once the head of the screw passes the band, the band automatically resiliently restores itself to the unflexed or less-flexed position over the head of the screw, illustrated in FIGS. 5 and 5B. Thus, in bone support assemblies of the invention, driving the bone screw, and thereby mounting the bone support assembly in the body of a recipient thereof, automatically flexes the band, as a locking member, out of the way of insertion of the bone screw, and then the locking member/band automatically flexes to a blocking position over the head or other break structure of the screw, thereby automatically activating the locking feature of the bone support assembly to lock the bone screw in the assembly. Such bone screw can, of course be released for removal by manually or otherwise intentionally flexing the band and removing the screw while the band is thus flexed.

In preferred embodiments of the invention, all of apertures 22 are slot-shaped in that each aperture has an elongate dimension and a shorter cross-dimension. Preferably, two of the apertures are relatively lesser lengths and serve as the support apertures, and the remaining apertures are relatively greater lengths, as slots, and serve as the settle apertures, providing for the bone to settle while being advantageously held by the bone support plate. As seen in FIGS. 1 and 2, typically each aperture along the length of the bone support assembly is progressively longer/shorter than the adjacent apertures in the same row. Typically bone support assemblies have two rows of apertures. And while the bone support assemblies illustrated in the drawings show 2 rows of bone screw apertures, the invention can well be utilized with any number of rows of apertures, and any number of apertures per row.

Further to other embodiments, bands 14 are shown with each band extending the full length of channel 26. It is contemplated that bands 14 can be segmented so as to comprehend 2 or more bands extending e.g. serially along one or both of side walls 30. For example, a separate band can be used in support of the function of each or any aperture.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A bone support assembly, comprising:
   (a) a bone support plate, said bone support plate comprising a top surface, a bottom surface opposite the top surface, a plurality of bone-fastener-receiving apertures for receiving bone fasteners therethrough for securing said bone support assembly to bone structure of a recipient; and
   (b) a substantially straight locking member mounted to said bone support plate and extending into a respective said bone-fastener-receiving aperture, said locking member being effective, when a bone fastener is driven through a said aperture into bone structure of a recipient, to automatically and as a consequence of driving such bone fastener, activate a locking feature of said bone support assembly effective to prevent the bone fastener from withdrawing out of said bone support assembly and past said locking member.

2. A bone support assembly as in claim 1 wherein first and second ones of said bone-fastener-receiving apertures comprise circular openings.

3. A bone support assembly as in claim 1 wherein all of said bone-fastener-receiving apertures comprise circular openings.

4. A bone support assembly as in claim 1, said locking member comprising a resiliently flexible band, said bone support assembly further comprising a band retainer mounted to said bone support plate, and retaining said flexible band to said bone support plate.

5. A bone support assembly as in claim 4 wherein said bone support plate comprises a retainer-receiving aperture extending through said bone support plate to the bottom surface of said bone support plate, further comprising a stud extending through said retainer-receiving aperture, said stud being secured to said bone support plate adjacent the bottom surface of said bone support plate, and securing said band retainer, and said resiliently flexible band, to said bone support plate.

6. A bone support assembly as in claim 4 wherein a portion of said band retainer overlies said flexible band, wherein said bone support plate comprises a stud-receiving aperture extending from the top surface of said bone support plate to the bottom surface of said bone support plate, further comprising a stud extending through said retainer-receiving aperture, said stud being welded to said bone support plate adjacent the bottom surface of said bone support plate, and securing said band retainer, and said flexible band, to said bone support plate.

7. A bone support assembly as in claim 4 wherein a portion of said band retainer overlies said flexible band, wherein said band retainer comprises an aperture therethrough, and wherein said bone support plate comprises an aperture underlying the aperture in said band retainer, and including a fastener extending through the aperture in said band retainer, and into the underlying aperture in said bone support plate, and thereby securing said band retainer to said bone support plate.

8. A bone support assembly as in claim 1 wherein the composition of said locking member comprises predominantly nickel and titanium.

9. A bone support assembly as in claim 1 wherein the composition of said locking member comprises about 55 percent by weight to about 56 percent by weight nickel and about 44 percent by weight to about 45 percent by weight titanium.

10. A bone support assembly as in claim 1 wherein the composition of said locking member comprises a shape memory metal alloy comprising predominantly nickel and titanium.

11. A bone support assembly as in claim 1, said locking member comprising a resiliently flexible band, a length of said band extending along a side of, and across a portion of, one or more corresponding ones of the apertures whereby, as such bone fastener is driven, a break structure of such bone fastener can urge said band to automatically flex, from a first flexural condition, until such break structure in such bone fastener is driven past said band, whereupon said band returns to the previous flexural condition and overlies said break structure of such so-driven bone fastener and thereby prevents such bone fastener from withdrawing from said bone support assembly.

12. A bone support assembly as in claim 1, said bone support plate further comprising a channel defined in and as part of the top surface of said bone support plate, the channel having side walls thereof opening into and extending alongside ones of said plurality of bone-fastener-receiving apertures, said locking member comprising a resiliently flexible band disposed in said channel and extending along a side of the channel.

13. A bone support assembly as in claim 1 wherein some of said bone-fastener-receiving apertures comprise slots, enabling longitudinal movement of bone fasteners in said slots, with respect to said bone support plate.

14. A bone support assembly, comprising:
   (a) a bone support plate, said bone support plate comprising a top surface, a bottom surface opposite the top surface, a plurality of bone-fastener-receiving apertures for receiving bone fasteners therethrough for securing said bone support assembly to bone structure of a recipient; and
   (b) a locking member mounted to said bone support plate at a location longitudinally displaced along said bone support plate from said apertures, said locking member being effective, when a bone fastener is driven through a said aperture into bone structure of a recipient, to automatically and as a consequence of driving such bone fastener, activate a locking feature thereof effective to prevent the bone fastener from withdrawing out of said bone support assembly and past said locking member,
   said locking member comprising a resiliently flexible band, a length of said band extending along a side of one or more corresponding ones of the apertures whereby, as such bone fastener is driven, a break structure of such bone fastener can urge said band to automatically flex, from a first flexural condition, until such break structure in such bone fastener is driven past the band, whereupon the band returns to the previous flexural condition and overlies the break structure of the so-driven bone fastener and thereby prevents the bone fastener from withdrawing.

15. A bone support assembly as in claim 14 wherein said flexible band extends along substantially a full length of said bone support plate.

16. A bone support assembly as in claim 14, including a second flexible band and wherein the first and second flexible bands collectively extend along the sides of all of the bone-fastener-receiving apertures.

17. A bone support assembly as in claim 16, further comprising a band retainer mounted to said bone support plate, and mounting said flexible bands to said bone support plate.

18. A bone support assembly as in claim 16 wherein the compositions of said flexible bands comprise predominantly nickel and titanium.

19. A bone support assembly as in claim 16 wherein the compositions of said flexible bands comprise about 55 percent by weight to about 56 percent by weight nickel and about 44 percent by weight to about 45 percent by weight titanium.

20. A bone support assembly as in claim 16 wherein the compositions of said flexible bands comprise a shape memory metal alloy comprising predominantly nickel and titanium.

21. A bone support assembly as in claim 16 wherein the compositions of said flexible bands are selected from the group consisting of titanium and stainless steel.

22. A bone support assembly as in claim 14 wherein the composition of said flexible band is not a shape memory metal alloy, and wherein said flexible band is sufficiently small in cross-section, and is properly positioned over a respective said aperture, so as to let such bone fastener pass below said flexible band, with flexing of said flexible band, and without exceeding a flexural limit of said flexible band, such that said flexible band then returns to a blocking position over such bone fastener.

23. A bone support assembly as in claim 14, further comprising a band retainer mounting said flexible band to said bone support plate at a locus away from a corresponding said bone-fastener-receiving aperture.

24. A bone support assembly, comprising:
(a) a bone support plate, said bone support plate comprising a top surface, a bottom surface opposite the top surface, a plurality of bone-fastener-receiving apertures for receiving bone fasteners therethrough for securing said bone support assembly to bone structure of a recipient; and
(b) a locking member mounted to said bone support plate, said locking member being effective, when a bone fastener is driven through a said aperture into bone structure of a recipient, to automatically and as a consequence of driving such bone fastener, activate a locking feature thereof effective to prevent the bone fastener from withdrawing out of said bone support assembly and past said locking member, said bone support plate further comprising a channel defined in and as part of the top surface of said bone support plate, the channel having side walls thereof opening into and extending alongside ones of said plurality of bone-fastener-receiving apertures, said locking member comprising a resiliently flexible band disposed in said channel and extending along a side of the channel.

25. A bone support assembly as in claim 24 wherein said channel has a bottom surface.

26. A bone support assembly as in claim 24, including a second flexible band and wherein the first and second flexible bands extend along substantially full lengths of respective firsthand second sides of the channel, said first and second flexible bands collectively extending along the sides of all of the bone-fastener-receiving apertures.

27. A bone support assembly as in claim 26, further comprising at least one band retainer mounted to said bone support plate, and retaining said flexible bands to said bone support plate, said band retainer urging said flexible bands against respective first and second sides of the channel.

28. A bone support assembly as in claim 26, further comprising at least one band retainer mounted to said bone support plate, and retaining said flexible bands to said bone support plate, said band retainer urging said flexible bands against respective first and second sides of the channel.

29. A bone support assembly as in claim 24, said bone support plate being elongate, said bone-fastener-receiving apertures being arrayed in first and second rows along a length of said bone support plate, said bone support assembly further comprising a second resiliently flexible band, wherein said first and second resiliently flexible bands are mounted at the opposing side walls of the channel, and extend along a portion of the length of the channel wherein the channel interfaces with the bone-fastener-receiving apertures.

30. A bone support assembly as in claim 29, said first and second bands being mounted to said bone support plate by at least one band retainer displaced from the apertures, whereby said first and second bands can flex at respective said apertures about mounting loci displaced longitudinally along said bone support plate from respective ones of the bone-fastener-receiving apertures, when bone fasteners are driven through the bone support plate and respectively past respective edges of said first and second bands.

31. A bone support assembly as in claim 30 wherein each said band is mounted to said bone support plate by a plurality of said band retainers disposed along a length of the respective band at loci displaced from respective said bone-fastener-receiving apertures.

32. A bone support assembly, comprising:
(a) a bone support plate, said bone support plate comprising a top surface, a bottom surface opposite the top surface, a plurality of bone-fastener-receiving apertures for receiving bone fasteners therethrough for securing said bone support assembly to bone structure of a recipient; and
(b) a locking member mounted to said bone support plate, said locking member being effective, when a bone fastener is driven through a said aperture into bone structure of a recipient, to automatically and as a consequence of driving such bone fastener, activate a locking feature thereof effective to prevent the bone fastener from withdrawing out of said bone support assembly and past said locking member, wherein at least some of said bone-fastener-receiving apertures comprise slots, and wherein the respective said slots have lengths greater than respective widths of the respective said slots, said slots enabling longitudinal movement of bone fasteners in said slots, with respect to said bone support plate.

33. A method of mounting a bone support assembly to bone structure, the method comprising
(a) providing a bone support assembly, comprising
(i) a bone support plate having a length, having a top surface, a bottom surface opposite the top surface, and a plurality of bone-fastener-receiving apertures for receiving bone fasteners therethrough for securing the bone support assembly to such bone structure of a recipient, and
(ii) one or more resiliently flexible bands mounted to the bone support plate, a length of the band extending along sides of corresponding ones of the apertures which are longitudinally spaced from each other along the length of the bone support plate; and
(b) driving a bone fastener through a respective bone-fastener-receiving aperture and including driving a break structure of the bone fastener past the flexible band such that the break structure of the fastener causes the flexible band to flex transversely of the length of the band, as the break structure of the bone fastener passes the band whereupon, when the break structure of the fastener moves past the flexible band, the resiliently flexible band returns from the flexing and overlies the break structure of the so-driven bone fastener, thereby preventing the bone fastener from withdrawing out of the bone support assembly past the resiliently flexible band.

34. A method as in claim 33, including providing a bone support plate which comprises a channel in the top surface of the bone support plate, the channel having opposing first and second sides, the channel opening into and extending alongside ones of the plurality of bone-fastener-receiving apertures, the one or more resiliently flexible bands being positioned in the channel along one or both sides of the channel and extending across portions of respective ones of the apertures.

35. A method as in claim 33, including driving a plurality of bone fasteners through respective bone-fastener-receiving apertures in the bone support plate, including driving each bone fastener a sufficient distance toward the bone support plate that a break structure on the respective fastener passes the flexible band whereby the flexible band flexes over the break surface of the fastener and thereby prevents the bone fastener from withdrawing out of the bone support assembly past the resiliently flexible band.

36. A bone support assembly, comprising:
(a) a bone support plate having a length, said bone support plate comprising a top surface, a bottom surface opposite the top surface, a plurality of bone-fastener-receiving apertures for receiving bone fasteners therethrough for securing said bone support assembly to bone structure of a recipient; and
(b) a locking member mounted to said bone support plate, and extending into a respective said bone-fastener-receiving aperture, a length of said locking member extending away from the respective said aperture and along the length of said bone support plate, said locking member being effective, when a bone fastener is driven through a said aperture into bone structure of a recipient, to automatically and as a consequence of driving such bone fastener, activate a locking feature of said bone support assembly, effective to prevent the bone fastener from withdrawing out of said bone support assembly and past said locking member.

37. A bone support assembly as in claim 36, said locking member comprising a resiliently flexible band, a length of said band extending along a side of, and across a portion of, one or more corresponding ones of the apertures whereby, as such bone fastener is driven, a break structure of such bone fastener can urge said band to automatically flex, from a first flexural condition, until such break structure in such bone fastener is driven past the band, whereupon the band returns to the previous flexural condition and overlies the break structure of the so-driven bone fastener and thereby prevents the bone fastener from withdrawing from said bone support assembly.

38. A bone support assembly as in claim 37, further comprising a band retainer mounting said flexible band to said bone support plate at a locus away from a corresponding said bone-fastener-receiving aperture.

39. A bone support assembly as in claim 37, including a second flexible band and wherein the first and second flexible bands collectively extend along the sides of, and across portions of, all of the bone-fastener-receiving apertures.

40. A bone support assembly as in claim 36, said bone support plate further comprising a channel defined in and as part of the top surface of said bone support plate, the channel having side walls thereof opening into and extending alongside ones of said plurality of bone-fastener-receiving apertures, said locking member comprising a resiliently flexible band disposed in said channel and extending along a side of the channel.

41. A bone support assembly as in claim 40 wherein said channel has a bottom surface.

42. A bone support assembly as in, claim 40 wherein said flexible band extends along substantially a full length of said bone support plate.

43. A bone support assembly as in claim 40, including a second flexible band and wherein the first and second flexible bands extend along substantially full lengths of respective first and second sides of the channel, said first and second flexible bands collectively extending along the sides of, and across portions of, all of the bone-fastener-receiving apertures.

44. A bone support assembly as in claim 43, further comprising at least one band retainer mounted to said bone support plate, and retaining said flexible bands to said bone support plate, said band retainer urging said flexible bands against respective first and second sides of the channel.

45. A bone support assembly as in claim 40, said bone support plate being elongate, said bone-fastener-receiving apertures being arrayed in first and second rows along the length of said bone support plate, said bone support assembly further comprising a second resiliently flexible band, wherein said first and second resiliently flexible bands are mounted along the opposing side walls of the channel, and extend along a portion of the length of the channel occupied by the bone-fastener-receiving apertures.

46. A bone support assembly as in claim 45, said first and second bands being mounted to said bone support plate by at least one band retainer displaced from the apertures, whereby said first and second bands can flex at respective said apertures about mounting loci displaced longitudinally along said bone support plate from respective ones of the bone-fastener-receiving apertures, when bone fasteners are driven through the bone support plate and respectively past respective edges of said first and second bands.

47. A bone support assembly as in claim 36 wherein at least some of said bone-fastener-receiving apertures comprise slots, enabling longitudinal movement of bone fasteners in said slots, with respect to said bone support plate.

48. A bone support assembly as in claim 36, said locking member comprising a resiliently flexible band, said bone support assembly further comprising a band retainer mounted to said bone support plate, and retaining said flexible band to said bone support plate.

49. A bone support assembly as in claim 48 wherein said bone support plate comprises a retainer-receiving aperture extending through said bone support plate to the bottom surface of said bone support plate, and wherein said band retainer comprises a stud extending through said retainer-receiving aperture, said stud being secured to said bone support plate adjacent the bottom surface of said bone support plate and securing said band retainer, and said resiliently flexible band, to said bone support plate.

50. A bone support assembly, comprising:
(a) a bone support plate having a length, said bone support plate comprising a top surface, a bottom surface opposite the top surface and adapted to engage bone structure of a recipient, a plurality of bone-fastener-receiving apertures for receiving bone fasteners therethrough for securing said bone support assembly to such bone structure of such recipient; and (b) a locking member mounted to said bone support plate, and extending alongside and into at least two of said bone-fastener-receiving apertures along the length of said bone support plate, said locking member being effective, when bone fasteners are driven through any of said at least two apertures and into bone structure of a recipient, to automatically and as a consequence of driving such bone fasteners, activate a locking feature of said bone support assembly, effective to prevent the bone fasteners from withdrawing out of said bone support assembly and past said locking member.

51. A bone support assembly as in claim 50, said locking member comprising a resiliently flexible band, a length of said band extending along a side of, and across at least a portion of, at least first and second ones of the apertures whereby, as a such bone fastener is driven through a respective one of the at least first and second apertures, a break structure of such bone fastener can urge said band to automatically flex, from a first flexural condition, until such break structure in such bone fastener is driven past said band, whereupon said band returns to the previous flexural condition and overlies such break structure of such so-driven bone fastener and thereby prevents the bone fastener from withdrawing from said bone support assembly.

52. A bone support assembly as in claim 51, further comprising a band retainer mounting said flexible band to said bone support plate at a locus away from a corresponding said bone-fastener-receiving aperture.

53. A bone support assembly as in claim 51 wherein said flexible band extends along substantially a full length of said bone support plate.

54. A bone support assembly as in claim 51, including a second flexible band and wherein the first and second flexible bands collectively extend along the sides of, and across portions of, all of the bone-fastener-receiving apertures.

55. A bone support assembly as in claim 50, said bone support plate further comprising a channel defined in and as part of the top surface of said bone support plate, the channel having side walls thereof opening into and extending alongside ones of said plurality of bone-fastener-receiving apertures, said locking member comprising a resiliently flexible band disposed in said channel and extending along a side of the channel.

56. A bone support assembly as in claim 55 wherein said channel has a bottom surface.

57. A bone support assembly as in claim 55, including a second flexible band and wherein the first and second flexible bands extend along substantially full lengths of respective first and second sides of the channel, said first and second flexible bands collectively extending along the sides of, and across portions of, all of the bone-fastener-receiving apertures.

58. A bone support assembly as in claim 57, further comprising at least one band retainer mounted to said bone support plate, and retaining said flexible bands to said bone support plate, said band retainer urging said flexible bands against respective first and second sides of the channel.

59. A bone support assembly as in claim 55, said bone support plate being elongate, said bone-fastener-receiving apertures being arrayed in first and second rows along a length of said bone support plate, said bone support assembly further comprising a second resiliently flexible band, wherein said first and second resiliently flexible bands are mounted at the opposing side walls of the channel, and extend along a portion of the length of the channel occupied by the bone-fastener-receiving apertures.

60. A bone support assembly as in claim 59, said first and second bands being mounted to said bone support plate by at least one band retainer displaced from the apertures, whereby said first and second bands can flex at respective said apertures about mounting loci displaced longitudinally along said bone support plate from respective ones of the bone-fastener-receiving apertures, when bone fasteners are driven through the bone support plate and respectively past respective ones of said first and second bands.

61. A bone support assembly as in claim 50 wherein at least some of said bone-fastener-receiving apertures comprise slots, enabling longitudinal movement of bone fasteners in said slots, with respect to said bone support plate.

62. A bone support assembly as in claim 50, said locking member comprising a resiliently flexible band, said bone support assembly further comprising a band retainer mounted to said bone support plate, and retaining said flexible band to said bone support plate.

63. A bone support assembly as in claim 62 wherein said bone support plate comprises a retainer-receiving aperture extending through said bone support plate to the bottom surface of said bone support plate, further comprising a stud extending through said retainer-receiving aperture, said stud being secured to said bone support plate adjacent the bottom surface of said bone support plate, and securing said band retainer, and said resiliently flexible band, to said bone support plate.

64. A bone support assembly, comprising:

(a) a bone support plate, said bone support plate comprising a length, a top surface, a bottom surface opposite the top surface, a plurality of bone-fastener-receiving apertures for receiving bone fasteners therethrough for securing said bone support assembly to bone structure of a recipient; and (b) locking structure mounted in said bone support plate assembly, and being disposed in channels which are expressed intermittently along the length of said bone support plate, including a length of said locking structure extending away from a respective said aperture, said locking structure being effective, when a bone fastener is driven through a said aperture into bone structure of a recipient user, to automatically and as a consequence of driving such bone fastener, activate a locking feature thereof effective to prevent the bone fastener from withdrawing out of said bone support assembly and past said locking member.

65. A bone support assembly as in claim 64, said locking member comprising a resiliently flexible band, a length of said band extending along a side of, and across a portion of one or more corresponding ones of the apertures whereby, as such bone fastener is driven, a break structure of such bone fastener can urge said band to automatically flex, from a first flexural condition, until such break structure in such bone fastener is driven past the band, whereupon the band returns to the previous flexural condition and overlies the break structure of the so-driven bone fastener and thereby prevents the bone fastener from withdrawing from said bone support assembly.

66. A bone support assembly as in claim 65, including a second flexible band and wherein the first and second flexible bands collectively extend along the sides of all of the bone-fastener-receiving apertures.

67. A bone support assembly as in claim 65, further comprising a band retainer mounting said flexible band to said bone support plate at a locus away from a corresponding said bone-fastener-receiving aperture.

68. A bone support assembly as in claim 64, the channel having side walls opening into and extending alongside ones of said plurality of bone-fastener-receiving apertures, said locking member comprising a resiliently flexible band disposed in the channel and extending along a side of the channel.

69. A bone support assembly as in claim 68, said bone support plate being elongate, said bone-fastener-receiving apertures being arrayed in first and second rows along the length of said bone support plate, said bone support assembly further comprising a second resiliently flexible band, wherein said first and second resiliently flexible bands are mounted at the opposing side walls of the channel, and extend along a portion of a length of the channel occupied by the bone-fastener-receiving apertures.

70. A bone support assembly as in claim 69, said first and second bands being mounted to said bone support plate by at least one band retainer displaced from the apertures, whereby said first and second bands can flex at respective said apertures about mounting loci displaced longitudinally along said bone support plate from respective ones of the bone-fastener-receiving apertures, when bone fasteners are driven through the bone support plate and respectively past said first and second bands.

71. A bone support assembly as in claim 64 wherein said channel has a bottom surface.

72. A bone support assembly as in claim 64 wherein at least some of said bone-fastener-receiving apertures comprise slots, enabling longitudinal movement of bone fasteners in said slots, with respect to said bone support plate.

73. A bone support assembly as in claim 64, said locking member comprising a resiliently flexible band, said bone support assembly further comprising a band retainer mounted to said bone support plate, and retaining said flexible band to said bone support plate.

74. A bone support assembly as in claim 73 wherein said bone support plate comprises a retainer-receiving aperture extending through said bone support plate to the bottom surface of said bone support plate, further comprising a stud extending through said retainer-receiving aperture, said stud being secured to said bone support plate adjacent the bottom surface of said bone support plate, and securing said band retainer, and said resiliently flexible band, to said bone support plate.

75. A bone support assembly, comprising:
(a) a bone support plate, said bone support plate comprising a top surface, a bottom surface opposite the top surface and adapted to engage bone structure of a recipient and, a plurality of bone-fastener-receiving apertures for receiving bone fasteners therethrough for securing said bone support assembly to such bone structure of such recipient; and
(b) a locking member mounted to said bone support plate, and extending into at least three of said bone-fastener-receiving apertures, said locking member being effective, when bone fasteners are driven through any of said at least three apertures and into bone structure of a recipient, to automatically and as a consequence of driving such bone fasteners, activate a locking feature of said bone support assembly, effective to prevent the bone fasteners from withdrawing out of said bone support assembly and past said locking member.

76. A bone support assembly as in claim 75, said locking member comprising a resiliently flexible band, a length of said band extending along sides of, and across portions of, longitudinally-displaced ones of the apertures whereby, as a such bone fastener is driven through a respective one of the at least three apertures, a break structure of such bone fastener can urge said band to automatically flex, from a first flexural condition, until such break structure in such bone fastener is driven past the band, whereupon the band returns to the previous flexural condition and overlies the break structure of the so-driven bone fastener and thereby prevents the bone fastener from withdrawing from said bone support assembly.

77. A bone support assembly as in claim 76 wherein said flexible band extends along substantially a full length of said bone support plate.

78. A bone support assembly as in claim 76, including a second flexible band and wherein the first and second flexible bands collectively extend along sides of all of the bone-fastener-receiving apertures.

79. A bone support assembly as in claim 76, further comprising a band retainer mounting said flexible band to said bone support plate at a locus away from a corresponding said bone-fastener-receiving aperture.

80. A bone support assembly as in claim 75, said bone support plate further comprising a channel comprising part of the top surface of said bone support plate, the channel having side walls opening into and extending alongside longitudinally spaced ones of said plurality of bone-fastener-receiving apertures, said locking member comprising a resiliently flexible band disposed in said channel and extending along a side of the channel.

81. A bone support assembly as in claim 80, including a second flexible band and wherein the first and second flexible bands extend along substantially full lengths of the side walls of the channel, said first and second flexible bands collectively extending along sides of all of the bone-fastener-receiving apertures.

82. A bone support assembly as in claim 81, further comprising at least one band retainer mounted to said bone support plate, and retaining said flexible bands to said bone support plate, said band retainer urging said flexible bands against respective first and second sides of the channel.

83. A bone support assembly as in claim 80, said bone support plate being elongate, said bone-fastener-receiving apertures being arrayed in first and second rows along a length of said bone support plate, said bone support assembly further comprising a second resiliently flexible band, wherein said first and second resiliently flexible bands are mounted at the opposing side walls of the channel, and extend along a portion of the length of the channel occupied by the bone-fastener-receiving apertures.

84. A bone support assembly as in claim 83, said first and second bands being mounted to said bone support plate by at least one band retainer displaced from the apertures, whereby said first and second bands can flex at respective said apertures about mounting loci displaced longitudinally along said bone support plate from respective ones of the bone-fastener-receiving apertures, when bone fasteners are driven through the bone support plate and respectively past respective said first and second bands.

85. A bone support assembly as in claim 75, wherein at least some of said bone-fastener-receiving apertures comprise slots, enabling longitudinal movement of bone fasteners in said slots, with respect to said bone support plate.

86. A bone support assembly as in claim 75, said locking member comprising a resiliently flexible band, said bone support assembly further comprising a band retainer mounted to said bone support plate, and retaining said flexible band to said bone support plate.

87. A bone support assembly as in claim 86 wherein said bone support plate comprises a retainer-receiving aperture extending through said bone support plate to the bottom surface of said bone support plate, further comprising a stud extending through said retainer-receiving aperture, said stud being secured to said bone support plate adjacent the bottom surface of said bone support plate, and securing said band retainer, and said resiliently flexible band, to said bone support plate.

88. A bone support assembly, comprising:
(a) a bone support plate having a length, said bone support plate comprising a top surface, a bottom surface opposite the top surface and adapted to engage bone structure of a recipient, and a plurality of bone-fastener-receiving apertures for receiving bone fasteners therethrough for securing said bone support assembly to such bone structure of such recipient; and
(b) a locking member mounted to said bone support plate, and extending into at least two of said bone-fastener-receiving apertures which are longitudinally spaced from each other along the length of said bone support plate, said locking member being effective, when bone fasteners are driven through any of said at least two apertures and into bone structure of a recipient, to automatically and as a consequence of driving such bone fasteners, activate a locking feature of said bone support assembly, effective to prevent the bone fasteners from withdrawing out of said bone support assembly and past said locking member.

89. A bone support assembly as in claim 88, said locking member comprising a resiliently flexible band, a length of said band extending along sides of, and across portions of, longitudinally-displaced ones of the apertures whereby, as a such bone-fastener is driven through a respective one of the at least two apertures, a break structure of such bone fastener urges said band to automatically flex, from a first flexural condition, until such break structure in such bone fastener is driven past the band, whereupon the band returns to the previous flexural condition and overlies the break structure of the so-driven bone fastener and thereby prevents the bone fastener from withdrawing from said bone support assembly.

90. A bone support assembly as in claim 89 wherein said flexible band extends along substantially a full length of said bone support plate.

91. A bone support assembly as in claim 89, including a second flexible band and wherein the first and second flexible bands collectively extend-along sides of all of the bone-fastener-receiving apertures.

92. A bone support assembly as in claim 89, further comprising a band retainer mounting said flexible band to said bone support plate at a locus away from a corresponding said bone-fastener-receiving aperture.

93. A bone support assembly as in claim 88, said bone support plate further comprising a channel comprising part of the top surface of said bone support plate, the channel having side walls opening into and extending alongside longitudinally spaced ones of said plurality of bone-fastener-receiving apertures, said locking member comprising a resiliently flexible band disposed in said channel and extending along a side of the channel.

94. A bone support assembly as in claim 93, including a second flexible band and wherein the first and second flexible bands/extend along substantially full lengths of the side walls of the channel, said first and second flexible bands collectively extending along sides of all of the bone-fastener-receiving apertures.

95. A bone support assembly as in claim 94, further comprising at least one band retainer mounted to said bone support plate, and retaining said flexible bands to said bone support plate, said band retainer urging said flexible bands against respective first and second sides of the channel.

96. A bone support assembly as in claim 95 wherein said bone support plate comprises a retainer-receiving aperture extending through said bone support plate to the bottom surface of said bone support plate, further comprising a stud extending through said retainer-receiving aperture, said stud being secured to said bone support plate adjacent the bottom surface of said bone support plate, and securing said band retainer, and said resiliently flexible band, to said bone support plate.

97. A bone support assembly as in claim 93, said bone support plate being elongate, said bone-fastener-receiving apertures being arrayed in first and second rows along a length of said bone support plate, said, bone support assembly further. comprising a second resiliently flexible band, wherein said first and second resiliently flexible bands are mounted at the opposing side walls of the channel, and extend along a portion of the length of the channel occupied by the bone-fastener-receiving apertures.

98. A bone support assembly as in claim 97, said first and second bands being mounted to said bone support plate by at least one band retainer displaced from the apertures, whereby said first and second bands can flex at respective said apertures about mounting loci displaced longitudinally along said bone support plate from respective ones of the bone-fastener-receiving apertures, when bone fasteners are driven through the bone support plate and respectively past respective said first and second bands.

99. A bone support assembly as in claim 88 wherein at least some of said bone-fastener-receiving apertures comprise slots, enabling longitudinal movement of bone fasteners in said slots, with respect to said bone support plate.

100. A bone support assembly as in claim 89, said locking member comprising a resiliently flexible band, said bone support assembly further comprising a band retainer mounted to said bone support plate, and retaining said flexible band to said bone support plate.

* * * * *